United States Patent [19]

Effland et al.

[11] 4,166,120

[45] Aug. 28, 1979

[54] ANALGESIC AND TRANQUILIZING BENZOYLPROPYL-SPIRO[DIHYDROBENZOFURAN]PIPERIDINES AND PYRROLIDINES

[75] Inventors: Richard C. Effland, Bridgewater; Joseph T. Strupczewski, Flemington; Beth A. Gardner, Succasunna, all of N.J.

[73] Assignee: American Hoechst Corporation, Bridgewater, N.J.

[21] Appl. No.: 896,584

[22] Filed: Apr. 14, 1978

[51] Int. Cl.$^2$ ............... A61K 31/445; A61K 31/40; C07D 491/10
[52] U.S. Cl. .................... 424/267; 260/326.5 R; 260/326.5 CA; 424/274; 546/17; 546/216
[58] Field of Search ............... 260/293.58, 293.66, 260/326.5 CA; 424/267, 274; 546/17

[56] References Cited

U.S. PATENT DOCUMENTS

| | | | |
|---|---|---|---|
| 2,500,714 | 3/1950 | Spielman | 260/293.58 |
| 3,649,635 | 3/1972 | Strandtman et al. | 260/326.14 |
| 3,850,938 | 11/1974 | Derible et al. | 260/293.61 |
| 3,962,259 | 6/1976 | Baver et al. | 546/17 |

OTHER PUBLICATIONS

Cram, D. et al., *Organic Chemistry*, McGraw Hill, New York, 1959, pp. 272–273.

March, J., *Advanced Organic Chemistry*, McGraw Hill, New York, 1968, p. 344.

*Primary Examiner*—Alan L. Rotman
*Assistant Examiner*—Richard A. Schwartz
*Attorney, Agent, or Firm*—Curtis, Morris & Safford

[57] ABSTRACT

Novel N-[3-benzoylpropyl]spiro[dihydrobenzofuran-piperidine and pyrrolidine]s and methods of preparing same are described. These compounds are useful as analgetics and tranquilizers.

27 Claims, No Drawings

ANALGESIC AND TRANQUILIZING BENZOYLPROPYL-SPIRO[DIHYDROBENZOFURAN]PIPERIDINES AND PYRROLIDINES

This invention relates to novel N-[3-(4-fluorobenzoyl)propyl]spiro[dihydrobenzofuran-piperidine and pyrrolidine]s, and the pharmaceutically acceptable acid addition salt thereof, which are useful as analgetics, tranquilizers, to methods of preparing the same, to methods of treatment with pharmaceutically effective amounts thereof and to pharmaceutical compositions containing such compounds as essential active ingredients.

The compounds of the invention have the formula

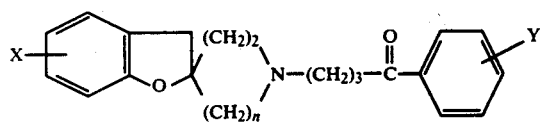

in which X is hydrogen, nitro, amino, halogen, methoxy or hydroxy; Y is nitro, amino, halogen, methoxy or hydroxy; and n is 1 or 2.

Acids useful for preparing the pharmaceutically acceptable acid salts of the invention include inorganic acids such as hydrochloric, hydrobromic, sulfuric, nitric, phoshoric and perchloric acids, as well as organic acids such as tartaric, citric, acetic, succinic, maleic and fumaric.

To the best of our knowledge the compounds of the present invention have not heretofore been described or suggested. Spiro[phthalanpiperidine]s of the formula

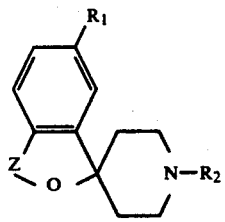

in which $R_1$ is hydrogen, loweralkyl, loweralkoxy, halogen or trifluoromethyl, $R_2$ is hydrogen or benzyl and Z is —$CH_2$— or —CO—, described by W. J. Houlihan et al. in U.S. Pat. No. 3,686,186 are outside the scope of this invention. The same applies to the natural product of the formula

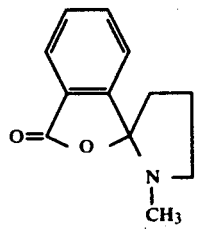

described by Y. Inubushi et al. [Chem. and Pharm. Bull (Japan) 12, 749 (1964)], as well as to substituted 1,3-dihydrospiro(isobenzofuran)s of the formula

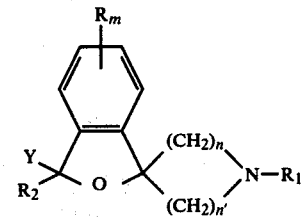

in which R is hydrogen, alkyl, alkoxy, trifluoromethyl, halogen, hydroxy or methylenedioxy; $R_1$ is hydrogen, alkyl, cycloalkylalkyl, alkenyl, phenylalkyl, diphenylalkyl, diphenylmethoxyalkyl, alkanoyl, phenylalkanoyl, benzoyl, benzoyalkyl, phenylhydroxyalkyl, alkoxycarbonyl, phenyloxycarbonyl or cycloalkylcarbonyl; $R_2$ is alkyl or phenyl; Y is hydrogen, alkyl, alkoxy, hydroxy or phenyl and m, n and n' are integers from 1 to 3; and to 1,3-dihydrospiro(isobenzofuran)s of the formula

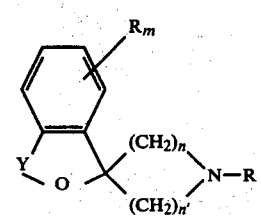

in which R is hydrogen, alkyl, alkoxy, trifluoromethyl, halogen, hydroxy or methylenedioxy; $R_1$ is alkyl, cycloalkylalkyl, phenylalkyl, diphenylalkyl, diphenylmethoxyalkyl, alkanoyl, phenylalkanoyl, benzoylalkyl, phenylhydroxyalkyl or cycloalkylcarbonyl; Y is $CH_2$ or CO; m is 1 or 2 and n and n' are integers from 1 to 3, described by Victor J. Bauer and Raymond W. Kosley, Jr. in U.S. Pat. Nos. 3,959,475 and 3,962,259, respectively.

The compounds of the invention are prepared by the sequence described below. In this description the definitions of X, Y and n are as defined earlier.

A. An N-unsubstituted spiro[dihydrobenzofuran-piperidine or pyrrolidine] of the formula

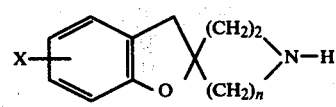

is reacted with a γ-chloro-butyrophenone ethylene glycol ketal of the formula

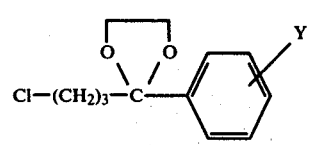

in a solvent to provide the corresponding intermediate compound of the invention of the formula

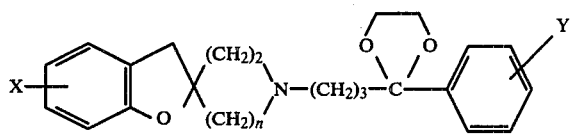

and likewise having analgetic and tranquilizing activity. Reaction temperatures can range from about 25° C. to reflux of the reaction mixture. Optionally, an acid scavenger such as potassium carbonate and a reaction initiator may be present in the reaction mixture. Preferred solvents are dimethylformamide and butyl alcohol.

B. The resulting ketal is subjected to hydrolysis, preferably with a strong acid such as 3 N hydrochloric acid in a solvent at about ambient temperature, to yield the corresponding N-[3-benzoylpropyl] compound of the invention.

C. An aforesaid compound of the invention in which X or Y or both are methoxy can be demethylated by any convenient method known to the art, preferably with 48% hydrobromic acid under reflux conditions, to produce the corresponding compound of the invention in which X or Y or both are hydroxy.

The N-unsubstituted precursor, utilized in Step A, can be prepared as follows:

1. A 2-fluorobenzyl chloride or bromide of the formula

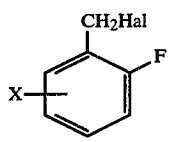

in which Hal is Cl or Br is converted to its Grignard reagent, preferably by use of ether as a solvent and a crystal of iodine to initiate the reaction. The Grignard reagent is reacted with a cycloazalkanone of the formula

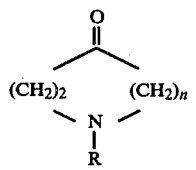

in which R can be alkyl, alkenyl, cycloalkylalkyl or phenylalkyl to provide a compound of the formula

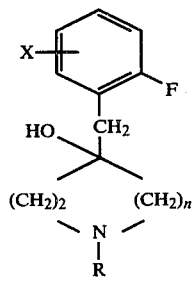

(I)

This is reacted with a non-nucleophilic base in the presence of a solvent at a temperature of from 25° C. to the reflux point of the solvent to provide a compound of the formula

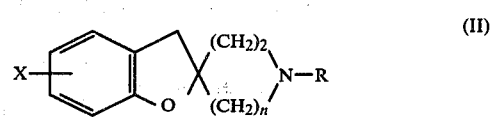

(II)

in which R is as defined above. In a preferred embodiment, sodium hydride is used as the base, dimethylformamide and benzene are used as a combined solvent and the temperature is the reflux temperature.

A compound conforming to formula II in which R is benzyl can be hydrogenated by any convenient method to provide the corresponding N-unsubstituted precursor. A preferred method involves hydrogenation with a palladium on carbon catalyst.

Alternatively, a compound of formula II can be treated with a chloroformate, e.g., an alkylchloroformate or phenylchloroformate, at a temperature of 25°–125° C. in a solvent such as toluene or benzene to provide the corresponding N-alkoxycarbonyl or N-phenoxycarbonyl compound.

Thereafter, said N-alkoxycarbonyl or N-phenoxycarbonyl compound is treated under reflux conditions with a base such as sodium or potassium hydroxide in a solvent such as water or ethanol, or with an acid such as hydrogen bromide in acetic acid to provide the N-unsubstituted precursor.

Also, a precursor in which X is hydrogen can be reacted in a known fashion, e.g., in a solvent such as pyridine or chloroform, with an alkanoyl halide or anhydride to provide the corresponding compound consistent with formula II in which R is alkanoyl and X is hydrogen. The use of an acid scavenger such as sodium bicarbonate, potassium carbonate or triethylamine is optional. The reaction temperature can vary from about 0° C. to the reflux point of the solvent, however, reflux conditions are preferred. The compound in which R is alkanoyl can be treated with a mixture of concentrated nitric acid in glacial acetic acid to provide the corresponding compound of the invention in which the 5-position of the ring structure is substituted by nitro. This reaction is carried out at a temperature ranging from 25° to 150° C., preferably 100° C.

Finally, an N-unsubstituted precursor in which X is $NO_2$ can be subjected to catalytic reduction to provide the corresponding compound of the invention in which X is amino. One such method involves hydrogenation under pressure with a Raney nickel catalyst.

The compounds of the present invention are useful as analgetics due to their ability to alleviate pain in mammals. This analgetic utility of compound of this invention is demonstrated in the phenyl-2-quinone writhing assay in mice, a standard assay for analgesia [Proc. Soc. Exptl. Biol. Med., 95, 729 (1957)]. Tabulated below are the percentages of inhibition of writhing accomplished with various subcutaneous dosages of representative compounds of the invention.

| Compound | Dose mg/kg | % Inhibition |
| --- | --- | --- |
| 2,3-dihydro-1'-[3-(4-fluorobenzoyl)-propyl]-5-nitrospiro[benzofuran-2,4'-piperidine]hydrochloride | 0.4 | 50 |
| 2,3-dihydro-1'-[3-(4-fluorobenzoyl)-propyl]-6-chlorospiro[benzofuran-2,4'- | | |

-continued

| Compound | Dose mg/kg | % Inhibition |
|---|---|---|
| piperidine]hydrochloride | 1.8 | 50 |
| 2,3-dihydro-1'-[3-(4-fluorobenzoyl)-propyl]-5-chlorospiro[benzofuran-2,4'-piperidine]hydrochloride | 1.7 | 50 |
| 2,3-dihydro-1'-[3-(4-fluorobenzoyl)-propyl]spiro[benzofuran-2,4'-piperidine]hydrochloride | 10 | 93 |
| | 6.0* | 50 |

*oral dosage

For comparison, aspirin and propoxyphene, known analgesic agents, effect a 34% and 50% inhibition at a dose of 60 mg/kg and 28 mg/kg, respectively. These data illustrate that the compounds of this invention are useful for alleviating pain in mammals when administered in amounts ranging from about 0.05 to about 100 mg/kg of body weight per day.

Compounds of the present invention are also useful as tranquilizers due to their ability to depress the central nervous system of mammals. This ability is demonstrated in the Sidman Avoidance Paradigim [Science, 118, 157–8 (1953)], a standard assay for tranquilizers, according to which an 11.1 mg/kg, intraperitoneal dose of 2,3-dihydro-1'-[3-(4-fluorobenzoyl)propyl]spiro[benzofuran-2,4'-piperidine]hydrochloride effects a 50% reduction in learned avoidance of electrical shock in rat. Compounds are useful as tranquilizers when administered in amounts ranging from 0.05 to about 100 mg/kg per day.

Other compounds of the invention include:
2,3-dihydro-5-amino-1'-[3-(4-fluorobenzoyl)propyl]-spiro[benzofuran-2,4'-piperidine];
2,3-dihydro-1'-[3-(4-fluorobenzoyl)propyl]-5-methoxyspiro[benzofuran-2,4'-piperidine];
2,3-dihydro-1'-[3-(4-fluorobenzoyl)propyl]-5-fluorospiro[benzofuran-2,4'-piperidine];
2,3-dihydro-1'-[3-(4-fluorobenzoyl)propyl]-6-methoxyspiro[benzofuran-2,3'-pyrrolidine];
2,3-dihydro-1'-[3-(4-fluorobenzoyl)propyl]-6-bromospiro[benzofuran-2,3'-pyrrolidine];
2,3-dihydro-1'-[3-(4-nitrobenzoyl)propyl]spiro[benzofuran-2,4'-piperidine];
2,3-dihydro-1'-[3-(4-methoxybenzoyl)propyl]spiro[benzofuran-2,4'-piperidine];
2,3-dihydro-1'-[3-(2-bromobenzoyl)propyl]spiro[benzofuran-2,4'-piperidine];
2,3-dihydro-1'-[3-(4-aminobenzoyl)propyl]spiro[benzofuran-2,4'-piperidine];
2,3-dihydro-1'-[3-(2-nitrobenzoyl)propyl]spiro[benzofuran-2,3'-pyrrolidine];
2,3-dihydro-1'-[3-(3-methoxybenzoyl)propyl]spiro[benzofuran-2,3'-pyrrolidine];
2,3-dihydro-1'-[3-(3-bromobenzoyl)propyl]spiro[benzofuran-2,3'-pyrrolidine];
2,3-dihydro-1'-[3-(4-bromobenzoyl)propyl]spiro[benzofuran-2,3'-pyrrolidine];
2,3-dihydro-1'-[3-(4-aminobenzoyl)propyl]spiro[benzofuran-2,3'-pyrrolidine];
2,3-dihydro-1'-[3-(4-hydroxybenzoyl)propyl]spiro[benzofuran-2,4'-piperidine];
2,3-dihydro-1'-[3-(2-hydroxybenzoyl)propyl]spiro[benzofuran-2,3'-pyrrolidine];
2,3-dihydro-5-hydroxy-1'-[3-(4-hydroxybenzoyl)-propyl]spiro[benzofuran-2,4'-piperidine];
2,3-dihydro-5-methoxy-1'-[3-(4-hydroxybenzoyl)-propyl]spiro[benzofuran-2,4'-piperidine];
2,3-dihydro-4-amino-1'-[3-(4-fluorobenzoyl)propyl]-spiro[benzofuran-2,4'-piperidine];
2,3-dihydro-1'-[3-(4-fluorobenzoyl)propyl]-4-methoxyspiro[benzofuran-2,3'-pyrrolidine];
2,3-dihydro-1'-[3-(4-fluorobenzoyl)propyl]-7-fluorospiro[benzofuran-2,4'-piperidine];
2,3-dihydro-1'-[3-(4-fluorobenzoyl)propyl]-7-nitrospiro[benzofuran-2,3'-pyrrolidine]; and
2,3-dihydro-7-chloro-1'-[3-(2-nitrobenzoyl)propyl]-spiro[benzofuran-2,4'-piperidine].

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservative dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied to between 0.5% and about 30% of the weight thereof. The amount of active compound in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The present invention is further illustrated by the following examples of representative compounds and procedures.

EXAMPLE 1

A. A few milliliters of 2-fluorobenzyl chloride (from a solution of 14.5 g of 2-fluorobenzyl chloride in 75 ml of ether) are added to a mixture of 2.7 g of magnesium shavings in 25 ml of ether containing a crystal of iodine. The reaction is initiated by warming gently with a hot air gun. After the reaction begins, the remainder of the 2-fluorobenzyl chloride solution is added dropwise while maintaining the reaction mixture at reflux. After total addition the reaction mixture is stirred at reflux for an additional 15 minutes before adding dropwise with vigorous stirring a solution of 25.0 g of N-benzyl-4-piperidone in 75 ml of ether. The resulting suspension is stirred at ambient temperature for about 2 hours and then filtered. The filter cake is washed thoroughly with ether before being hydrolyzed by stirring with an ammonium chloride solution. The aqueous mixture is extracted with ether, the combined ether extracts are dried and then the ether is removed, leaving a yellow-green oil. The oil is purified by distillation, leaving a yellow oil which solidifies upon standing to the light yellow solid, 1-benzyl-4-(2-fluorobenzyl)-4-piperidinol.

B. A solution of 6.9 g of 1-benzyl-4-(2-fluorobenzyl)-4-piperidinol in 25 ml of dimethylformamide and 10 ml of benzene is added to a stirred suspension of 1.4 g of 50% sodium hydride in 50 ml of dimethylformamide and 10 ml of benzene. The mixture is heated at 110°–120° C. for 5 hours with an air condenser to allow evaporation of the benzene. Thereafter, the mixture is permitted to cool to ambient temperature. The cooled mixture is poured over ice, diluted with water and then extracted with ether. The ether phase is washed successively with water and a saturated sodium chloride aqueous solution and then dried. The ether is removed from the dried solution, leaving an oil which solidifies on standing to a light yellow solid. The solid is dissolved in ether where it is treated with ethereal hydrogen chloride to give a salt as a white solid. The solid is recrystallized from isopropyl alcohol to provide white crystals, 2,3-dihydro-1'-benzylspiro[benzofuran-2,4'-piperidine]-hydrochloride, mp 246°–247° C.

Analysis: Calculated for $C_{19}H_{21}NO \cdot HCl$: 72.24%, C; 7.03%, H; 4.44%, N. Found: 71.95%, C; 7.06%, H; 4.34%, N.

C. A solution of 5.3 g of 2,3-dihydro-1'-benzylspiro[benzofuran-2,4'-piperidine], free base of B, in 250 ml of isopropyl alcohol is hydrogenated with a Paar shaker, 50 psig, 65°–70° C. and 1 g of a 10% palladium/carbon catalyst until the uptake of hydrogen is completed. Thereafter, the solution is successively permitted to cool to ambient temperature, filtered and concentrated to dryness, leaving a white solid. The solid is dissolved in a benzene-ether mixture, the solution filtered through celite and then concentrated again providing a white solid, which upon trituration with ether, provides the product, 2,3-dihydrospiro[benzofuran-2,4'-piperidine], mp 56°–58.5° C.

Analysis: Calculated for $C_{12}H_{15}NO$: 76.14%, C; 8.00%, H; 7.40%, N. Found: 76.05%, C; 8.08%, H; 7.27%, N.

D. A solution of 5.0 g of 2,3-dihydrospiro[benzofuran-2,4'-piperidine], 8.3 g of potassium carbonate, 5.0 g of potassium iodide, and 7.1 g of γ-chloro-p-fluorobutyrophenone ethylene glycol ketal in 75 mls of dimethylformamide is stirred for 18 hours at 90° C. Thereafter, the reaction mixture is permitted to cool to ambient temperature before evaporating off the excess solvent providing a light tan semi-solid. This residue is dissolved in benzene in which it is washed successively with water and a saturated saline solution, and then the benzene is evaporated off leaving a dark oil. The oil is dissolved in a solution of 75 ml of methyl alcohol and 40 ml of 3 N hydrochloric acid and this solution is stirred at ambient temperature for 24 hours.

Thereafter, the reaction solution is sequentially basified with 2 N sodium hydroxide, extracted twice with chloroform, and dried. The chloroform is evaporated off leaving an oil which is dissolved in ether, where it is converted to a hydrogen chloride salt, a white precipitate. The salt is recrystallized thrice from ethyl alcohol to give the product, 2,3-dihydro-1'-[3-(4-fluorobenzoyl)propyl]spiro[benzofuran-2,4'-piperidine]-hydrochloride, mp 232°–235° C.

Analysis: Calculated for $C_{22}H_{24}FNO_2 \cdot HCl$: 67.77%, C; 6.46%, H; 3.59%, N; 9.09%, Cl; 4.87%, F. Found: 67.98%, C; 6.65%, H; 3.68%, N; 9.20%, Cl; 5.10%, F.

EXAMPLE 2

A. A crystal of iodine followed by a few mls of a solution of 20.6 g of 2-fluorobenzyl chloride in 100 ml of ether is added to a suspension of 3.4 g of magnesium shavings in 50 ml of ether. Thereafter, the reaction is initiated via a hot air gun before adding dropwise, while maintaining the reaction at reflux, the remaining 2-fluorobenzyl chloride solution. After total addition, the reaction is maintained at reflux with stirring for an additional hour before successively adding 100 ml of ether and adding dropwise, with vigorous stirring, a solution of 25.0 g of N-benzyl-3-pyrrolidinone in 100 ml of ether. After complete addition, the resulting suspension is refluxed for an additional 2 hours, stirred at ambient temperature for 16 more hours, and then filtered. The filter cake is washed well with ether and then hydrolyzed by stirring in an ice-ammonium chloride solution. The aqueous solution is extracted thrice with ether and the combined ether extracts are washed successively with water and a sodium chloride solution and then dried. The solvent is removed and the residue is distilled at 135°–140° C., 0.1 mm pressure, to provide a viscous yellow oil which solidifies upon standing. The solid is recrystallized twice from an ethanol-water mixture to give the product, 1-benzyl-3-(2-fluorobenzyl)-3-pyrrolidinol, mp 75°–77° C.

B. 38.1 g of 1-benzyl-4-(2-fluorobenzyl)-3-pyrrolidinol dissolved in 125 ml of benzene and 125 ml of dimethylformamide are added dropwise to a stirred suspension of 4.7 g of sodium hydride in 125 ml benzene and 125 ml of dimethylformamide, at 90° C. After total addition, the reaction is stirred at 90° C. for 120 hours and then permitted to cool to ambient temperature prior to being poured into 1 liter of ice water. The biphasic mixture is extracted with ether and the combined ether extracts are dried and then evaporated, leaving a dark oil. The oil is distilled at 170°–175° C., 0.1 mm pressure, leaving 24 g of a light yellow oil which solidifies on standing. The solid is recrystallized twice from isopropyl alcohol leaving the product, 2,3-dihydro-1'-benzylspiro[benzofuran-2,3'-pyrrolidine], mp 43°–45° C.

Analysis: Calculated for $C_{18}H_{19}NO$: 81.47%, C; 7.22%, H; 5.28%, N. Found: 81.59%, C; 7.39%, H; 5.16%, N.

C. A solution of 21.4 g of 2,3-dihydro-1'-benzylspiro[benzofuran-2,3'-pyrrolidine] and 200 ml of isopropyl alcohol is hydrogenated over 2.0 g of a 10% palladium on carbon catalyst at 45 psig at 50° C. until the uptake of hydrogen is completed. Thereafter, the reaction mixture is filtered and concentrated under reduced pressure leaving a yellow oil. The oil is dissolved in ether where it is converted to its hydrogen chloride salt. The salt is recrystallized twice from an ethyl alcohol-ether mixture to provide the product, 2,3-dihydrospiro[benzofuran-2,3'-pyrrolidine]hydrochloride, mp 174°–178° C.

Analysis: Calculated for $C_{11}H_{13}NO.HCl$: 62.41%, C; 6.67%, H; 6.62%, N; 16.75%, Cl. Found: 62.17%, C; 6.72%, H; 6.58%, N; 16.60%, Cl.

D. A solution of 7.2 g of 2,3-dihydrospiro[benzofuran-2,4'-pyrrolidine], free base of C, 14 g of potassium carbonate, a few grains of potassium iodide and 11 g of γ-chloro-p-fluorobutyrophenone ethylene glycol ketal in 100 ml of dimethylformamide, is heated at 100° C. for 2.5 hours. Thereafter, the reaction solution is permitted to cool to ambient temperature before being filtered and concentrated to dryness, leaving a dark oil. The oil is dissolved in 100 ml of methyl alcohol and 50 ml of 3 N hydrochloric acid and this solution is stirred for 18 hours. The well stirred solution is sequentially basified with 3 N sodium hydroxide and extracted with chloroform. The chloroform extracts are dried before being evaporated to dryness, leaving a dark oil which is purified on a silica gel column, a 3% methyl alcohol in chloroform eluant. The purified oil is dissolved in ether where it is converted to its oxalic acid salt, a white precipitate. The salt is recrystallized once from an ethyl alcohol-ether mixture and then 4 times from ethyl alcohol to provide the product, 2,3-dihydro-1'-[3-(4-fluorobenzoyl)propyl]spiro[benzofuran-2,3-pyrrolidine]oxalate hydrate, mp 93°–95° C.

Analysis: Calculated for $C_{21}H_{22}FNO_2.(CO_2H)_2.H_2O$: 61.73%, C; 5.85%, H; 3.13%, N. Found: 61.96%, C; 5.48%, H; 3.02%, N.

EXAMPLE 3

A. A sample of 4-chloro-2-fluorobenzyl bromide is converted to its Grignard reagent which is reacted with N-benzyl-4-piperidone to provide 1-benzyl-4-(4-chloro-2-fluorobenzyl)-4-piperidinol. The above is performed in a manner consistent with the procedure of Example 2A. This product is distilled at 175°–180° C., 0.18 mm to provide an orange oil which is converted in ether to its hydrogen chloride salt. The salt is recrystallized four times from an ethyl alcohol-ether mixture to provide the purified salt, m.p. 211.5°–213° C.

B. A solution of 8.3 g of 1-benzyl-4-(4-chloro-2-fluorobenzyl)-4-piperidinol in 75 ml of benzene is added dropwise to a stirred suspension at ambient temperature of 1.5 g of sodium hydride (50% oil dispersion) in 100 ml of benzene. After total addition, the reaction mixture is brought to reflux before adding 35 ml of dimethylformamide. Thereafter, the reaction mixture is sequentially refluxed for 15 minutes, cooled to ambient temperature, and diluted by the dropwise addition of 100 ml of water. The reaction mixture is poured into 1 liter of ice-water and extracted three times with ether. The combined ether extracts are successively washed with a saturated sodium chloride solution, dried and the ether is then removed under reduced pressure, leaving an oil. The oil is boiled in hexane and the hexane removed, leaving a yellow oil which solidifies upon standing. The oil is dissolved in ether where it is converted to its hydrogen chloride salt. The salt is recrystallized thrice from an ethyl alcohol-ether mixture to provide the product 2,3-dihydro-1'-benzyl-6-chlorospiro[benzofuran-2,4'-piperidine]hydrochloride, mp 257°–259° C.

Analysis: Calculated for $C_{19}H_{20}ClNO.HCl$: 65.15%, C; 6.04%, H; 4.00%, N; 20.24%, Cl. Found: 65.01%, C; 6.07%, H; 4.05%, N; 20.11%, Cl.

C. A stirred solution of 6.1 g of 2,3-dihydro-1'-benzyl-6-chlorospiro[benzofuran-2,4'-piperidine], free base of B and 2.5 g of ethylchloroformate in 150 ml of benzene, is refluxed for 18 hours. Thereafter, the solution is successively permitted to cool to ambient temperature, washed with water, washed with a saturated sodium bicarbonate solution, washed with a saturated sodium chloride solution, dried and concentrated to dryness leaving a dark oil. The oil is taken up in a mixture of 50 ml of a 50% potassium hydroxide solution and 100 ml of ethyl alcohol, and this mixture is refluxed for 18 hours and then permitted to cool to room temperature before removal of the ethyl alcohol under reduced pressure. The remaining aqueous suspension is extracted with ether and the combined ether extracts are washed with 3 N hydrochloric acid. The acidic wash is basified with 6 N sodium hydroxide and the basified solution is extracted with ether. The combined ether extracts are dried before being concentrated to dryness, which leaves an off-white solid. The solid is dissolved in ether where it is converted to its hydrogen chloride salt which is recrystallized twice from ethyl alcohol providing the product, 2,3-dihydro-6-chlorospiro[benzofuran-2,4'-piperidine]hydrochloride, mp 281°–288° C.

Analysis: Calculated for $C_{12}H_{14}ClNO.HCl$: 55.40%, C; 5.81%, H; 5.38%, N; 27.26%, Cl. Found: 55.21%, C; 5.86%, H; 5.38%, N; 27.07%, Cl.

D. A mixture of 2.7 g of 2,3-dihydro-5-chlorospiro[benzofuran-2,4'-piperidine], free base of C, 1.5 g of potassium carbonate, a few grains of potassium iodide and 3.5 g of γ-chloro-p-fluorobutyrophenone ethylene glycol ketal in 100 ml of n-butyl alcohol, is refluxed for 24 hours. Thereafter, the reaction solution is permitted to cool and then filtered. The filtered solution is evaporated to dryness leaving a dark oil, which is dissolved in 100 ml of methyl alcohol and 50 ml of 3 N hydrochloric acid and then this solution is stirred for 18 hours. The reaction mixture is basified with a 6 N sodium hydroxide solution and then extracted with ethyl acetate. The ethyl acetate extracts are sequentially washed with brine, dried and evaporated to dryness, leaving an oil which solidifies upon standing to a tan solid. The solid is purified on a silica gel column with a 2% methyl alcohol in chloroform eluant. The chromatographed solid is dissolved in ether where it is converted to its hydrochloric acid salt, a white precipitate. The salt is recrystallized twice from an ethyl alcohol-ether mixture to provide the product, 2,3-dihydro-1'-[3-(4-fluorobenzoyl)propyl]-6-chlorospiro[benzofuran-2,4'-piperidine]-hydrochloride, mp 253°–255° C.

Analysis: Calculated for $C_{22}H_{23}ClFNO_2 \cdot HCl$: 62.27%, C; 5.70%, H; 3.30%, N. Found: 62.23%, C; 5.78%, H; 3.38%, N.

EXAMPLE 4

A. A sample of 5-chloro-2-fluorobenzyl bromide is converted to its Grignard reagent which is reacted with N-benzyl-4-piperidone to provide 1-benzyl-4-(5-chloro-2-fluorobenzyl)-4-piperidinol. The above is performed in a manner consistent with the procedure of Example 2A. This product is distilled at 210° C., 0.15 mm giving an orange oil. The oil is dissolved in ether where it is converted to its hydrochloride salt which is recrystallized thrice from an ethyl alcohol-ether mixture to provide the product, 1-benzyl-4-(5-chloro-2-fluorobenzyl)-4-piperidinol hydrochloride, mp 217°–219° C.

B. A sample of 1-benzyl-4-(5-chloro-2-fluorobenzyl)-4-piperidinol, free base of A, is treated in a manner consistent with Example 3B, to provide the salt, 2,3-dihydro-1'-benzyl-5-chlorospiro[benzofuran-2,4'-piperidine]hydrochloride.

Analysis: Calculated for $C_{19}H_{20}ClNO \cdot HCl$: 65.15%, C; 6.04%, H; 4.00%, N; 20.24%, Cl. Found: 65.21%, C; 6.11%, H; 3.98%, N; 20.06%, Cl.

C. A sample of 2,3-dihydro-1'-benzyl-5-chlorospiro[benzofuran-2,4'-piperidine] and free base of Example B is treated in a manner consistent with the procedure of Example 3C to provide the product 2,3-dihydro-5-chlorospiro[benzofuran-2,4'-piperidine]hydrochloride, mp 217°–218° C. This product is obtained after three recrystallizations, two from ethyl alcohol and then one from an ethyl alcohol-ether mixture.

Analysis: Calculated for $C_{14}H_{14}ClNO_4 \cdot HCl$: 55.40%, C; 5.81%, H; 5.38%, N; 27.26%, Cl. Found: 55.53%, C; 5.84%, H; 5.40%, N; 27.11%, Cl.

D. A stirred mixture of 7.0 g of 2,3-dihydro-5-chlorospiro[benzofuran-2,4'-piperidine], free base of C, 10 g of potassium carbonate and 8.9 g of γ-chloro-p-fluorobutyrophenone ethylene glycol ketal in 250 ml of n-butyl alcohol is treated and worked up according to the manipulative procedure of Example 3 to provide the product, 2,3-dihydro-1'-[3-(4-fluorobenzoyl)propyl]-5-chlorospiro[benzofuran-2,4'-piperidine]hydrochloride, mp 241°–243° C.

Analysis: Calculated for $C_{22}H_{23}ClFNO_2 \cdot HCl$: 62.27%, C; 5.70%, H; 3.30%, N; 16.71%, Cl. Found: 62.46%, C; 5.72%, H; 3.32%, N; 16.91%, Cl.

EXAMPLE 5

A. 3 ml of acetyl chloride in 10 ml of chloroform is added dropwise to a stirred suspension of 6.0 g of 2,3-dihydrospiro[benzofuran-2,4'-piperidine], Example 1C, and 14.0 g of sodium bicarbonate in 75 ml of chloroform. After total addition, the reaction mixture is successively stirred at ambient temperature for 16 hours, filtered, washed sequentially with water, dilute hydrochloric acid and a saturated sodium chloride solution, dried and the solvent removed under reduced pressure, leaving a residue which solidifies upon standing. The solid is recrystallized twice from hexane to give the product, 2,3-dihydro-1'-acetylspiro[benzofuran-2,4'-piperidine], mp 94°–97° C.

Analysis: Calculated for $C_{14}H_{17}NO_2$: 72.70%, C; 7.41%, H; 6.05%, N. Found: 72.85%, C; 7.47%, H; 6.08%, N.

B. 3.8 g of nitric acid (sp gr 1.42) in 30 ml of glacial acetic acid is added dropwise to a stirred solution of 4.7 g of 2,3-dihydro-1'-acetylspiro[benzofuran-2,4'-piperidine] in 65 ml of glacial acetic acid. After total addition, the reaction mixture is slowly heated to 100° C. over a 2 hour span and then cooled and poured into 500 ml of water. The diluted mixture is extracted with chloroform and the chloroform extracts are washed sequentially with a saturated sodium bicarbonate solution, a saturated sodium chloride solution and then dried. The chloroform is removed under reduced pressure. The residue is triturated with ether causing an orange precipitate, which is collected and recrystallized first from an ethyl alcohol-ether mixture and then from ethyl alcohol to provide the product, 2,3-dihydro-1'-acetyl-5-nitrospiro[benzofuran-2,4'-piperidine], mp 149°–150° C.

Analysis: Calculated for $C_{14}H_{16}N_2O_2$: 60.86%, C; 5.84%, H; 10.14%, N. Found: 60.83%, C; 5.82%, H; 10.14%, N.

C. A solution of 3.4 g of 2,3-dihydro-1'-acetyl-5-nitrospiro[benzofuran-2,4'-piperidine] in 150 ml of 6 N hydrochloric acid is refluxed for 45 hours and then stirred at ambient temperature for 16 hours. Thereafter, the reaction mixture is successively extracted once with ether, basified with 6 N sodium hydroxide and extracted thrice with ether. The combined ether extracts are dried and the solvent removed, leaving a yellow residue. The residue is dissolved in ether where it is converted to its hydrogen chloride salt. The salt is collected, dried and finally recrystallized twice from ethyl alcohol to give the product 2,3-dihydro-5-nitrospiro[benzofuran-2,4'-piperidine]hydrochloride, mp 265°–266° C.

Analysis: Calculated for $C_{12}H_{14}N_2O_3 \cdot HCl$: 53.24%, C; 5.59%, H; 10.35%, N. Found: 53.36%, C; 5.77%, H; 10.28%, N.

D. A stirred suspension of 5.2 g of 2,3-dihydro-5-nitrospiro[benzofuran-2,4'-piperidine] free base of C, 7.0 g of potassium carbonate, a few grains of potassium iodide and 6.2 g of γ-chloro-p-fluorobutyrophenone ethylene ketal in 200 ml of n-butyl alcohol is refluxed for 24 hours. Thereafter, the reaction mixture is permitted to cool to ambient temperature and then filtered. The filtrate is evaporated to dryness, leaving a brown oil. The oil is dissolved in 200 ml of methyl alcohol and 100 ml of 3N hydrochloric acid and this solution is stirred at ambient temperature for 18 hours and then basified with 6 N sodium hydroxide. The alkaline mixture is extracted with ethyl acetate and the ethyl acetate extracts are successively dried and evaporated to dryness, leaving an oil. The oil is chromatographed on a silica gel column eluting with chloroform which leads to a solid. The solid is dissolved in ether where it is converted to its hydrochloric acid salt, a white precipitate. The precipitate is recrystallized twice from ethyl alcohol to give the product 2,3-dihydro-1'-[3-(4-fluorobenzoyl)propyl]-5-nitrospiro[benzofuran-2,4'-piperidine]hydrochloride, mp 245°–247° C.

Analysis: Calculated for $C_{22}H_{23}FN_2O_4 \cdot HCl$: 60.76%, C; 5.56%, H; 6.44%, N. Found: 60.95%, C; 5.61%, H; 6.45%, N.

The other compounds of the invention can be prepared in a manner consistent with the foregoing examples.

We claim:

1. A compound depicted by the formula

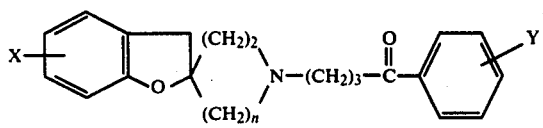

or a pharmaceutically acceptable acid addition salt thereof in which X is hydrogen, nitro, amino, halogen, methoxy or hydroxy; Y is nitro, amino, halogen, methoxy or hydroxy; and n is the integer 1 or 2.

2. A compound defined in claim 1 in which n is 2.

3. A compound defined in claim 1 in which n is 1.

4. A compound defined in claim 1 in which X is hydrogen, nitro, or chloro and Y is fluorine attached at the 4 position.

5. A compound defined in claim 4 in which n is 2.

6. A compound defined in claim 4 in which n is 1.

7. The compound defined in claim 1 which is 2,3-dihydro-1'-[3-(4-fluorobenzoyl)propyl]spiro[benzofuran-2,4'-piperidine] or a pharmaceutically acceptable acid addition salt thereof.

8. The compound defined in claim 1 which is 2,3-dihydro-1'-[3-(4-fluorobenzoyl)propyl]spiro[benzofuran-2,3'-pyrrolidine] or a pharmaceutically acceptable acid addition salt thereof.

9. The compound defined in claim 1 which is 2,3-dihydro-1'-[3-(4-fluorobenzoyl)propyl]-6-chlorospiro[benzofuran-2,4'-piperidine] or a pharmaceutically acceptable acid addition salt thereof.

10. The compound defined in claim 1 which is 2,3-dihydro1'-[3-(4-fluorobenzoyl)propyl]-5-chlorospiro[benzofuran-2,4'-piperidine] or a pharmaceutically acceptable acid addition salt thereof.

11. The compound defined in claim 1 which is 2,3-dihydro-1'-[3-(4-fluorobenzoyl)propyl]-5-nitrospiro[benzofuran-2,4'-piperidine] or a pharmaceutically acceptable acid addition salt thereof.

12. A compound of the formula

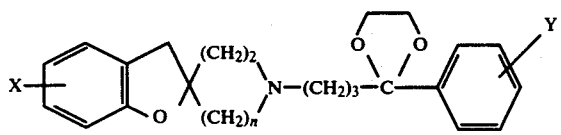

in which X is hydrogen, nitro, amino, halogen, methoxy, or hydroxy; Y is nitro, amino, halogen, methoxy or hydroxy and n is 1 or 2.

13. A compound according to claim 12 in which n is 2.

14. A compound according to claim 12 in which n is 1.

15. A compound according to claim 12 in which X is hydrogen, nitro or chlorine and Y is fluorine attached at the 4-position.

16. A compound according to claim 15 in which n is 2.

17. A compound according to claim 15 in which n is 1.

18. An analgesic or tranquilizer composition comprising between 0.5 and 70% by weight of a compound defined in claim 1 and a pharmaceutically acceptable carrier therefor.

19. An analgesic or tranquilizer composition comprising a pharmaceutically acceptable inert carrier and an effective analgesic or tranquilizing amount of a compound as defined in claim 7.

20. An analgesic or tranquilizer composition comprising a pharmaceutically acceptable inert carrier and an effective analgesic or tranquilizing amount of a compound as defined in claim 8.

21. An analgesic or tranquilizer composition comprising a pharmaceutically acceptable inert carrier and an effective analgesic or tranquilizing amount of a compound as defined in claim 9.

22. An analgesic or tranquilizer composition comprising a pharmaceutically acceptable inert carrier and an effective analgesic or tranquilizing amount of a compound as defined in claim 10.

23. An analgesic or tranquilizer composition comprising a pharmaceutically acceptable inert carrier and an effective analgesic or tranquilizing amount of a compound as defined in claim 11.

24. A method of alleviating pain in a patient which comprises administering to a patient an analgesically effective amount of a compound defined in claim 1.

25. A method of tranquilizing a patient which comprises administering to a patient an effective tranquilizing amount of a compound defined in claim 1.

26. The method as defined in claim 24 wherein said amount of said compound is from 0.05 to 300 mg/kg of body weight per day.

27. The method as defined in claim 25 wherein said amount of said compound is from 0.05 to 300 mg/kg of body weight per day.

* * * * *